United States Patent
Shiels et al.

(10) Patent No.: US 10,687,824 B2
(45) Date of Patent: Jun. 23, 2020

(54) SURGICAL SAW AND SAW BLADE FOR USE THEREWITH

(71) Applicant: Stryker European Holdings I, LLC, Kalamazoo, MI (US)

(72) Inventors: Paul Shiels, Albuquerque, NM (US); Seamus Gilhooley, Galway (IE)

(73) Assignee: Stryker European Holdings I, LLC, Kalamazoo, MI (US)

(*) Notice: Subject to any disclaimer, the term of this patent is extended or adjusted under 35 U.S.C. 154(b) by 34 days.

(21) Appl. No.: 16/040,898

(22) Filed: Jul. 20, 2018

(65) Prior Publication Data
US 2019/0021745 A1    Jan. 24, 2019

Related U.S. Application Data

(60) Provisional application No. 62/535,599, filed on Jul. 21, 2017.

(51) Int. Cl.
*A61B 17/14* (2006.01)
(52) U.S. Cl.
CPC .................................. *A61B 17/142* (2016.11)
(58) Field of Classification Search
CPC .............................. A61B 17/14; A61B 17/142
See application file for complete search history.

(56) References Cited

U.S. PATENT DOCUMENTS

| | | | |
|---|---|---|---|
| 3,384,085 A | 5/1968 | Hall | |
| RE27,032 E | 1/1971 | Hall | |
| 3,964,163 A | 6/1976 | Russo | |
| 4,157,231 A | 6/1979 | Phillips | |
| 4,637,391 A | 1/1987 | Schlein | |
| 4,985,031 A | 1/1991 | Buss et al. | |
| 5,147,364 A | 9/1992 | Comparetto | |
| 5,178,626 A | 1/1993 | Pappas | |
| 5,306,285 A * | 4/1994 | Miller | B23D 61/006 30/355 |
| 5,395,377 A | 3/1995 | Petersen et al. | |

(Continued)

FOREIGN PATENT DOCUMENTS

| | | |
|---|---|---|
| CN | 204218977 U | 3/2015 |
| EP | 1880682 A2 | 1/2008 |
| JP | 2002349959 | 12/2002 |

OTHER PUBLICATIONS

English language abstract and machine-assisted English translation for CN 204218977 extracted from espacenet.com database on Aug. 10, 2017, 5 pages.

(Continued)

*Primary Examiner* — Eric S Gibson
(74) *Attorney, Agent, or Firm* — Howard & Howard Attorneys PLLC (57) ABSTRACT

A surgical saw blade for being coupled to a drive hub of a surgical saw assembly. The blade includes an attachment portion configured to be removably coupled to the drive hub and a cutting portion opposite the attachment portion. The cutting portion includes a plurality of teeth. The blade also includes a pivot portion configured to engage a pivot structure of the surgical saw assembly. Additionally, the cutting portion has a follower which engages a blade support of the surgical saw assembly and is configured to limit deflection of the blade during use.

11 Claims, 9 Drawing Sheets

(56) References Cited

U.S. PATENT DOCUMENTS

| | | | |
|---|---|---|---|
| 5,423,845 A * | 6/1995 | McDaniel | B23D 61/121 30/355 |
| 5,496,316 A | 3/1996 | Goris | |
| 5,496,325 A | 3/1996 | McLees | |
| 5,507,763 A * | 4/1996 | Petersen | A61B 17/142 30/166.3 |
| 5,533,842 A | 7/1996 | Johnson et al. | |
| 5,578,039 A | 11/1996 | Vendrely et al. | |
| 5,653,714 A | 8/1997 | Dietz et al. | |
| 5,735,866 A * | 4/1998 | Adams | B23D 61/006 30/339 |
| 5,779,702 A | 7/1998 | Fard | |
| 6,022,353 A | 2/2000 | Fletcher et al. | |
| 6,342,057 B1 | 1/2002 | Brace et al. | |
| 7,691,106 B2 * | 4/2010 | Schenberger | A61B 17/142 606/82 |
| 7,901,424 B2 | 3/2011 | Fletcher et al. | |
| 8,052,692 B2 | 11/2011 | Lionberger et al. | |
| 8,100,912 B2 | 1/2012 | Marietta | |
| 8,246,620 B2 | 8/2012 | Holko et al. | |
| 8,323,285 B2 * | 12/2012 | Walen | A61B 17/142 29/428 |
| 8,491,596 B2 | 7/2013 | Long et al. | |
| 8,672,943 B2 * | 3/2014 | Fisher | A61B 17/142 606/82 |
| 8,685,028 B2 * | 4/2014 | Kim | A61B 17/142 606/82 |
| 8,734,450 B2 * | 5/2014 | Landon | A61B 17/142 30/337 |
| 8,814,872 B2 | 8/2014 | Bickenbach | |
| 8,888,783 B2 | 11/2014 | Young | |
| 8,939,981 B1 | 1/2015 | Anderson | |
| 9,033,986 B2 * | 5/2015 | Nelson | A61B 17/1624 606/171 |
| 9,119,631 B1 | 9/2015 | Murphy | |
| 9,414,845 B2 | 8/2016 | Boykin | |
| 9,439,655 B2 * | 9/2016 | Cosgrove | A61B 17/142 |
| 9,468,445 B2 * | 10/2016 | McGinley | A61B 17/15 |
| 9,498,231 B2 | 11/2016 | Haider et al. | |
| 2003/0236522 A1 | 12/2003 | Long et al. | |
| 2004/0098000 A1 * | 5/2004 | Kleinwaechter | B23D 61/006 D24/146 |
| 2006/0009796 A1 * | 1/2006 | Carusillo | A61B 17/157 606/178 |
| 2008/0027442 A1 | 1/2008 | Blue | |
| 2008/0119860 A1 * | 5/2008 | McCarthy | A61B 17/15 606/87 |
| 2008/0243125 A1 * | 10/2008 | Guzman | A61B 17/142 606/82 |
| 2009/0138017 A1 * | 5/2009 | Carusillo | A61B 17/157 606/82 |
| 2009/0182338 A1 * | 7/2009 | Walen | A61B 17/142 606/82 |
| 2010/0292701 A1 * | 11/2010 | Fisher | A61B 17/142 606/82 |
| 2012/0041443 A1 * | 2/2012 | Landon | A61B 17/142 606/82 |
| 2012/0089012 A1 | 4/2012 | Baur et al. | |
| 2012/0123418 A1 * | 5/2012 | Giurgi | A61B 17/16 606/80 |
| 2012/0130380 A1 | 5/2012 | Babaev | |
| 2012/0143196 A1 * | 6/2012 | Kim | A61B 17/142 606/82 |
| 2014/0163558 A1 * | 6/2014 | Cosgrove | A61B 17/142 606/82 |
| 2015/0020671 A1 * | 1/2015 | Meindorfer | B26D 7/086 83/697 |
| 2017/0027586 A1 * | 2/2017 | Ferro | A61B 17/142 |
| 2017/0348007 A1 * | 12/2017 | Shiels | A61B 17/142 |
| 2018/0064448 A1 * | 3/2018 | Mac an Tuile | B23D 51/16 |
| 2019/0021745 A1 * | 1/2019 | Shiels | A61B 17/142 |

OTHER PUBLICATIONS

English language abstract and machine-assisted English translation for EP 1 880 682 extracted from espacenet.com database on Aug. 29, 2018, 33 pages.

English language abstract and machine-assisted English translation of JP 2002-349959 extracted from espacenet.com database on Aug. 10, 2017, 10 pages.

Stryker Instruments, "Cutting Accessories", published at least as early as Jun. 3, 2016, pp. 5-7.

\* cited by examiner

SURGICAL SAW AND SAW BLADE FOR USE THEREWITH

RELATED APPLICATIONS

This application claims the benefit of and priority to U.S. Provisional Patent Application No. 62/535,599, filed on Jul. 21, 2017, the entire contents and disclosure of which are hereby incorporated herein by reference.

TECHNICAL FIELD

The embodiments described herein generally relate to surgical saws and saw blades for use therewith.

BACKGROUND

It is prevalent to use powered surgical saws during surgical procedures. Generally, these surgical saws have a handpiece which may include an electric or pneumatic motor disposed within the handpiece. A driver is operatively coupled to the motor to be driven in an oscillating manner by the motor. An attachment portion of a surgical saw blade is releasably coupled to the driver. At the opposite end of the blade is a cutting portion which includes teeth. The blade may be provided in various configurations including straight, crescentic, or other configurations. Additionally, the blade may be attached to the driver in various locations and positions. The blades may be disposable.

In conventional surgical saws, the blade rotates about a pivot axis adjacent a proximal end of the attachment portion. This configuration produces excessive inertia to be overcome by the motor which may necessitate a relatively large motor.

A surgical saw and blades for use therewith designed to overcome one or more of the aforementioned challenges is desired.

SUMMARY

In one embodiment, a surgical saw blade is provided for coupling to a drive hub of a surgical saw assembly. The saw blade comprises an attachment portion configured to be removably coupled to the drive hub. The saw blade also has a cutting portion opposite the attachment portion. The cutting portion includes a plurality of teeth. A pivot portion is configured to engage a pivot structure of the surgical saw assembly. The cutting portion has a follower which engages a blade support of the surgical saw assembly and is configured to limit deflection of the blade.

In another embodiment, a surgical saw assembly is provided. The surgical saw assembly comprises a housing and a driver disposed within the housing and having a drive hub. The driver is configured to be coupled to a motor. The surgical saw assembly further comprises a blade support including a pivot structure. A blade is configured to be removably coupled to the drive hub at an attachment portion. The blade has a cutting portion opposite the attachment portion. The cutting portion includes a plurality of teeth. The blade also has a pivot portion configured to be coupled to the pivot structure. The cutting portion has a follower configured to engage the blade support to limit deflection of the blade.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

Figure 1:
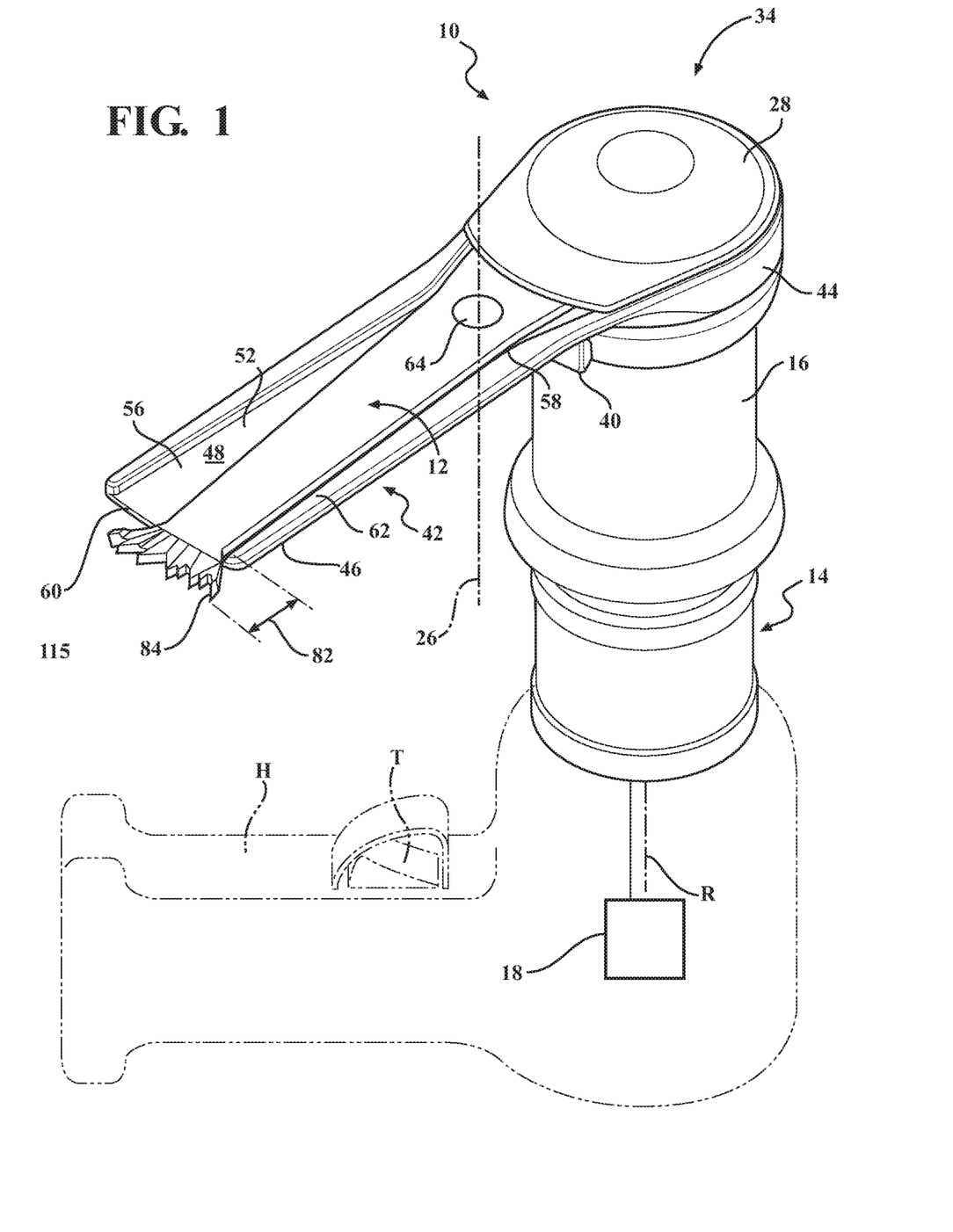
FIG. 1 is a perspective view of a surgical saw assembly having a lid in a closed position.
Figure 2:
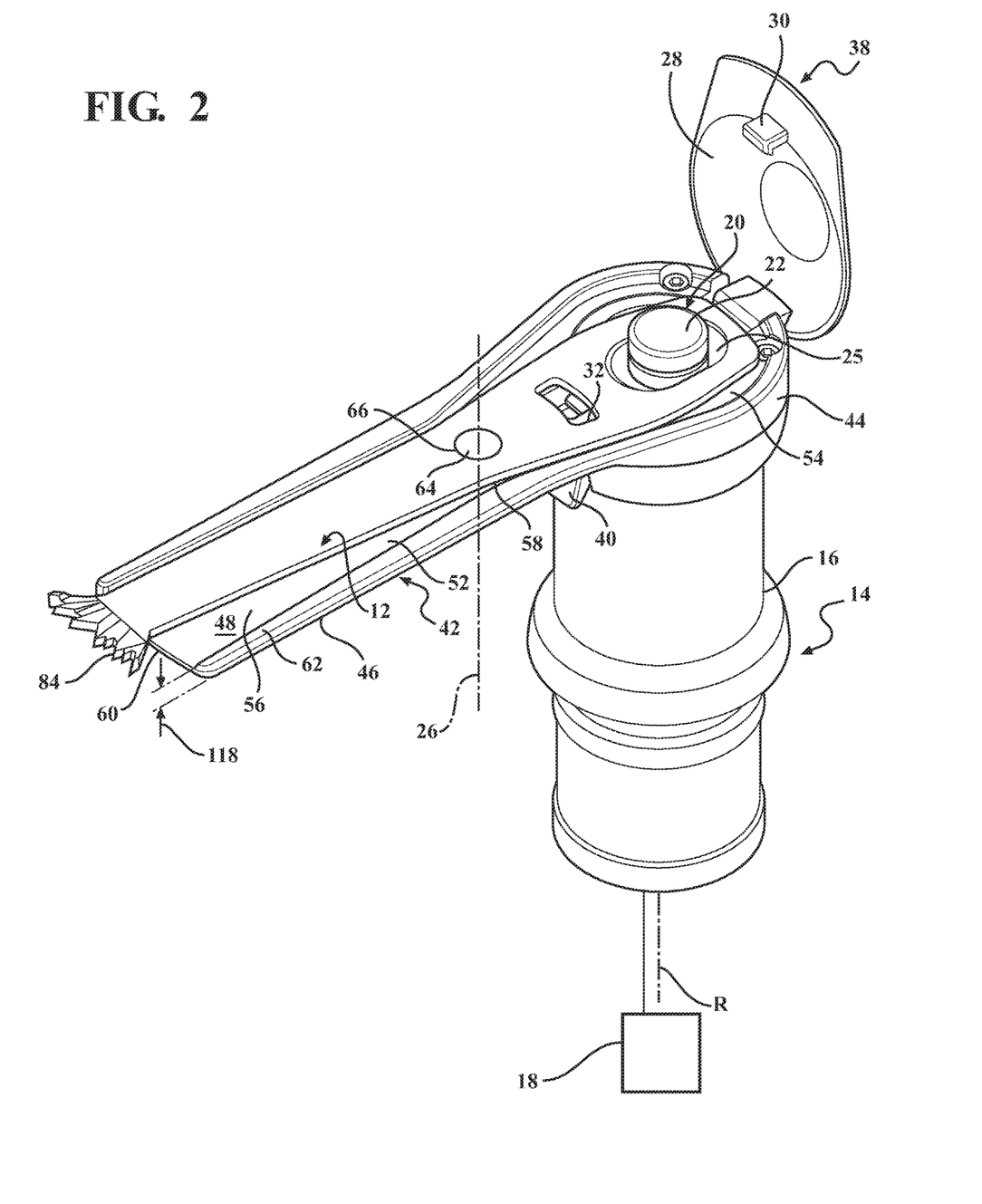
FIG. 2 is a perspective view of the surgical saw assembly having the lid in an open position.
Figure 3:
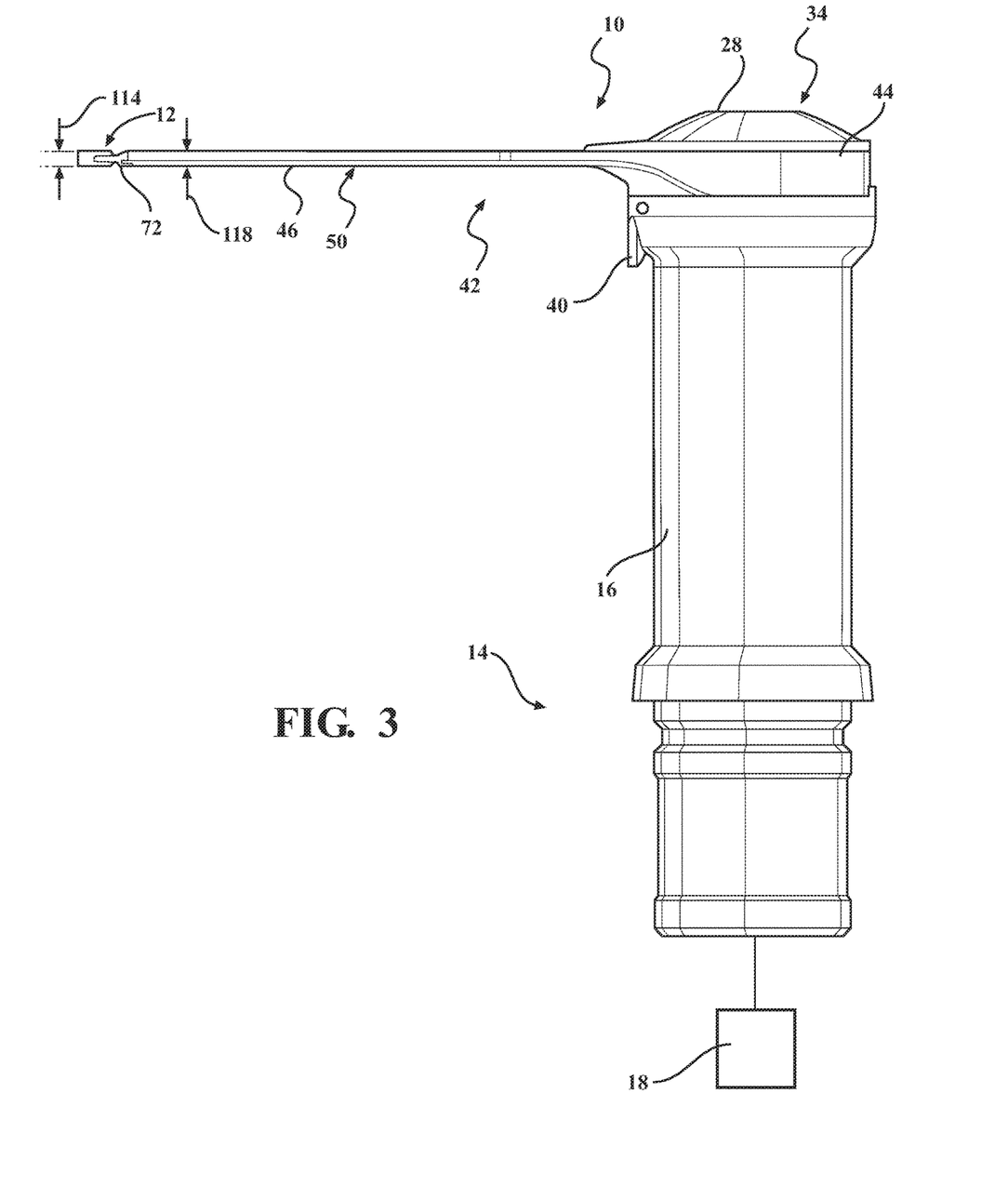
FIG. 3 is a side view of the surgical saw assembly.

Referring to FIGS. 1-3, a surgical saw assembly 10 is shown for use during surgical procedures. The surgical procedures may be orthopedic surgeries, brain surgeries, cardiovascular surgeries or any other surgeries requiring the use of a cutting instrument. The surgical saw assembly 10 includes a surgical saw blade 12. The blade 12 may be of various shapes and sizes such as a crescentic blade or a straight blade. The surgical saw assembly 10 shown in FIG. 1 has a straight coupler 14 for attaching to a handpiece H, such as a manually supported and manually manipulated handpiece, or a handpiece forming part of an end effector of a surgical robotic arm (not shown). The handpiece H is shown schematically in FIG. 1 to include a trigger T. It is also contemplated that the coupler 14 may be a right angle coupler or another type of coupler.

The coupler 14 comprises a housing 16 for attaching to the handpiece H. A motor 18 may be located in the handpiece H or in the housing 16 attached to the handpiece H. The motor 18 may be of any suitable type, including but not limited to a pneumatic or electrical motor. The motor 18 is configured to provide oscillating motion to the blade 12. It is contemplated that the motor 18 may provide cyclical linear motion and/or cyclical angular motion, such as used for an oscillating sagittal saw. The motor 18 may be operated via the trigger T and/or in an automated manner, using an on-board controller, an off-board control console, a robotic controller, or other type of control.

The motor 18 is operatively coupled to a driver 20 (See FIG. 2) to rotate the driver 20 about a rotational axis R. The driver 20 transfers drive torque from the motor 18 to the blade 12 to oscillate the blade 12. The driver 20 is at least partially disposed within the housing 16 and includes a drive hub 22. The drive hub 22 is configured to releasably receive the blade 12. As illustrated in FIGS. 1 and 2, the drive hub 22 may include one or more primary drive bosses adapted to engage the blade 12. In the embodiment illustrated in FIG. 2, the drive hub 22 includes a primary drive boss configured to act directly on the blade 12. The drive hub 22 is disposed through a hub aperture 25 defined through the blade 12. The drive hub 22 may comprise a roller bearing or other structure to reduce wear that could be caused by engagement with the blade 12 during operation.

The driver 20 oscillates the blade 12 about an axis of blade rotation 26 (also referred to as pivot axis 26). The drive hub 22 is shown eccentrically located on a shaft of the driver 20 relative to the rotational axis R. As a result, rotation of the driver 20 about the rotational axis R causes eccentric motion of the drive hub 22 and corresponding oscillation of the blade 12. The hub aperture 25 is elongated in size and shaped to accommodate such eccentric movement of the drive hub 22 to cause oscillation.

As illustrated in FIGS. 1-4, the blade 12 may be secured to the driver 20 using a lid 28. The lid 28 is adapted to be pivotally coupled to the housing 16 or a blade support 42 described below. The lid 28 may have a semi-circular portion as illustrated in the embodiment shown in FIG. 1, or may be any other shape including oval, rectangular, or the like. It is contemplated that the lid 28 is configured to help hold the blade 12 on the drive hub 22.

Figure 4A:
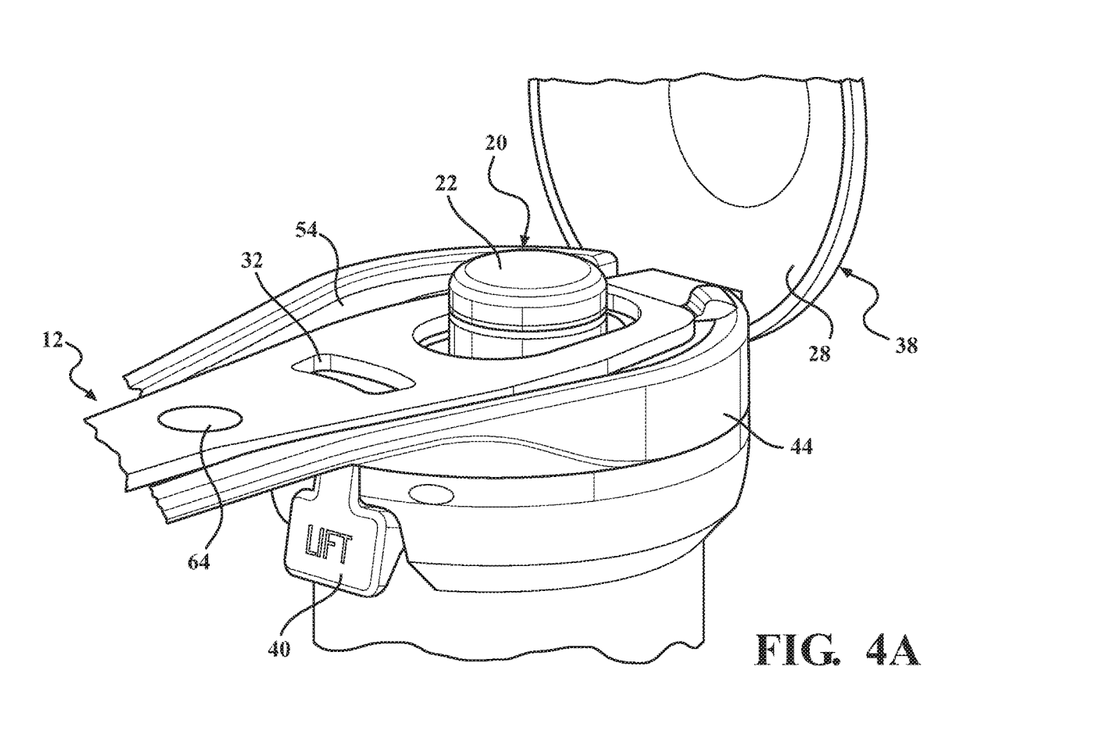
FIG. 4A is a perspective view of a portion of the surgical saw assembly.
Figure 4B:
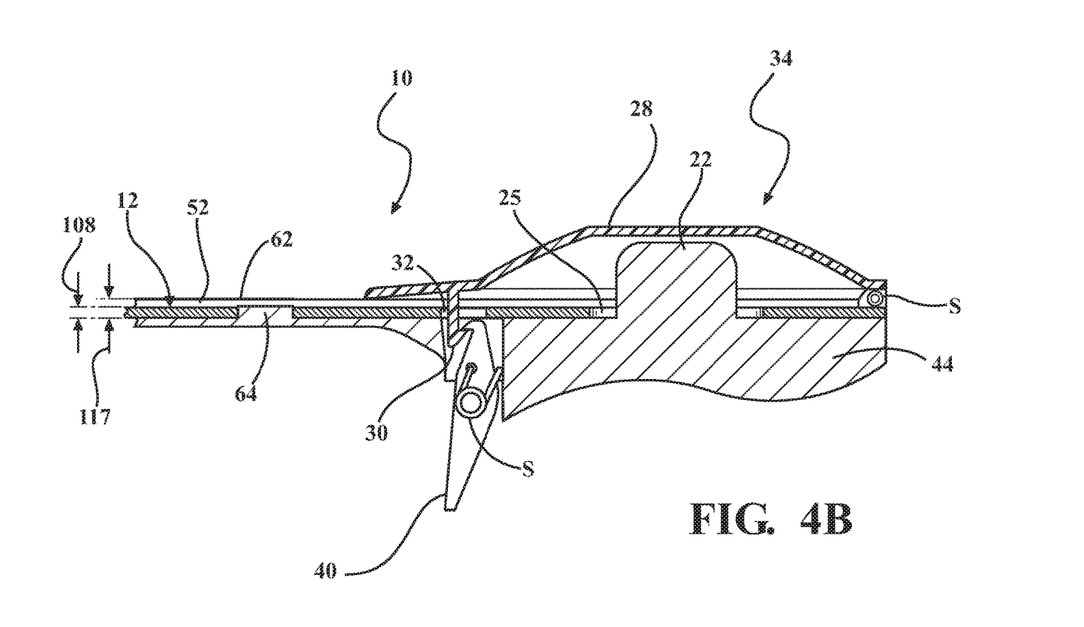
FIG. 4B is a cross-sectional view of the surgical saw assembly.

The lid 28 includes a protrusion 30 which is configured to be disposed through a securing aperture 32 in the blade 12 when the lid 28 is in a closed position 34. The protrusion 30 is further configured to engage a latch in order to securely maintain the lid 28 in the closed position 34, as best illustrated in FIG. 4B. If the blade 12 is being removed or an operator would like to otherwise open the lid 28, the latch 40 may be manually actuated to disengage the latch 40 from the protrusion 30 and allow the lid 28 to be moved from the closed position 34 to an open position 38. A spring S may bias the latch 40 into an engaged position. It is further contemplated that the lid 28 may be spring biased towards the open position 38 by another spring S, and the latch 40 is a lift-to-release latch pivotally coupled to the housing 16 or the blade support 42 described below. However, it is also contemplated that the latch 40 may be another type of latch and/or may be located in any position on the surgical saw assembly 10.

The surgical saw assembly 10 also includes the blade support 42 which extends from the housing 16 and is configured to support the blade 12. In the embodiment illustrated in FIGS. 1-3 the blade support 42 is fixed from movement relative to the housing 16 and extends perpendicularly to the housing 16, however, it is also contemplated that the blade support 42 could extend at another angle as desired. In some embodiments, the blade support 42 can be integrally formed with the housing 16. The blade support 42 may be comprised of plastic. It is also contemplated that the blade support 42 may be comprised of steel, a metal composite, or other material with suitable strength to support the blade 12 during operation of the surgical saw assembly 10.

In the embodiment illustrated, the blade support 42 includes a rounded end portion 44 which is coupled to and disposed directly above the housing 16. The rounded end portion 44 has a similar circumference to the housing 16 such that the circumference of the blade support 42 is in line with the circumference of the housing 16 to provide support for the blade 12 and also to provide a clean look to the surgical saw assembly 10. The blade support 42 extends from the housing 16 into an extension portion 46 which extends at a length less than or equal to a length of the blade 12. As illustrated in FIG. 2, the extension portion 46 of the blade support 42 is elongated and has a consistent width, however, it is contemplated that the extension portion 46 of the blade support 42 may be of varying width depending on the type/shape of the blade 12, desired range of oscillation of the blade 12, and/or other factors.

The blade support 42 includes a planar top surface 48 and a bottom surface 50 (see FIG. 3). As illustrated in FIGS. 1 and 2, the blade support 42 defines a channel 52. The channel 52 may be of various sizes and shapes and is configured to receive the blade 12 and allow oscillating movement of the blade 12. Referring to FIG. 2, the channel 52 has a rounded end channel portion 54, an extension channel portion 56, and a necked portion 58 therebetween. The lid 28 is sized and shaped to cover the rounded end channel portion 54, while the extension channel portion 56 remains uncovered. In the embodiment shown, the extension channel portion 56 is elongated and the lid 28 is sized to cover less than one-half of the channel 52, and may cover less than one-third of the channel 52 in other versions. The channel 52 widens from the necked portion 58 toward a distal end 60 of the blade support 42. The channel 52 is sized to neatly accommodate the range of oscillation of the blade 12. It is contemplated that various other channel configurations and sizes may be employed based on the desired blade shape, type, size, range of oscillation, and/or other factors.

Referring still to the embodiment illustrated in FIGS. 1 and 2, the blade support 42 has a shoulder 62 forming sides of the channel 52. The top surface 48 of the blade support 42 is defined inside the shoulder 62. The shoulder 62 may have varying width such that some portions of the shoulder 62 are wider than others. In the embodiment illustrated in FIGS. 1 and 2, the shoulder 62 of the blade support 42 is generally symmetrical on either side of a longitudinal axis of the blade support 42. However, it is also contemplated that the shoulder 62 may be asymmetrical. Additionally, the distal end 60 of the blade support 42 lacks a shoulder 62 such that the channel 52 is open at the distal end 60.

As best illustrated in FIG. 2, the blade support 42 includes a pivot structure 64 which is disposed within the channel 52. The pivot structure 64 is configured to engage the blade 12. More specifically, the blade 12 includes a pivot aperture 66 which is configured to receive the pivot structure 64 therethrough. In the embodiment shown, the pivot structure 64 is a round shaped protrusion (e.g. pivot pin or boss) extending approximately perpendicular from the top surface 48 of the blade support 42. The pivot structure 64 may be an integral, fixed part of the blade support 42 or may rotate with the blade 12 about the pivot axis 26 relative to the top surface 48. The blade 12 is configured to pivot about the pivot structure 64 within the channel 52. The pivot structure 64 has a flat top and has a height approximately equal to a thickness 108 (see FIG. 7) of the blade 12 such that the flat top is even with or slightly elevated above a top surface of the blade 12 when the blade 12 is in use. In the embodiment illustrated in FIGS. 1 and 2, the pivot structure 64 is disposed approximately centrally in the channel 52 with respect to a width of the channel 52 and slightly off-center in the channel 52 with respect to a length of the channel 52. However, it is contemplated that the pivot structure 64 may be disposed at another location within the channel 52. In some cases, by virtue of the pivot structure 52 being located closer to a longitudinal mid-point of the blade 12, than adjacent its proximal end 92 (see FIG. 7), inertia is reduced, which can reduce vibrations. In other embodiments, the pivot structure 52 is located so that pivoting of the blade 12 occurs closer to a distal end of the blade than the proximal end 92.

Figure 5:
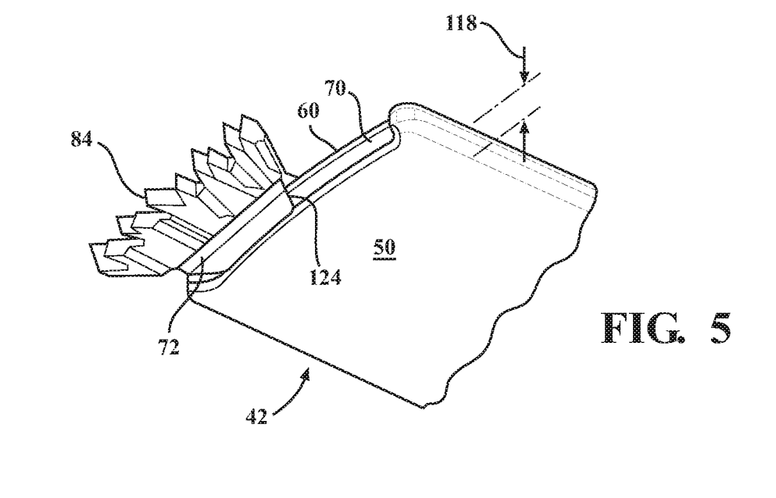
FIG. 5 is a bottom perspective view of a portion of the surgical saw assembly.

As best illustrated in FIG. 5, the blade support 42 also includes a support flange 70 defined at the distal end 60. The support flange 70 is configured to receive a follower 72 of the blade 12 and to allow the follower 72 of the blade 12 to ride/slide along the support flange 70. The support flange 70 may be slightly curved along the distal end 60 of the blade support 42 to accommodate arcuate travel of the follower 72 described further below.

Figure 7:
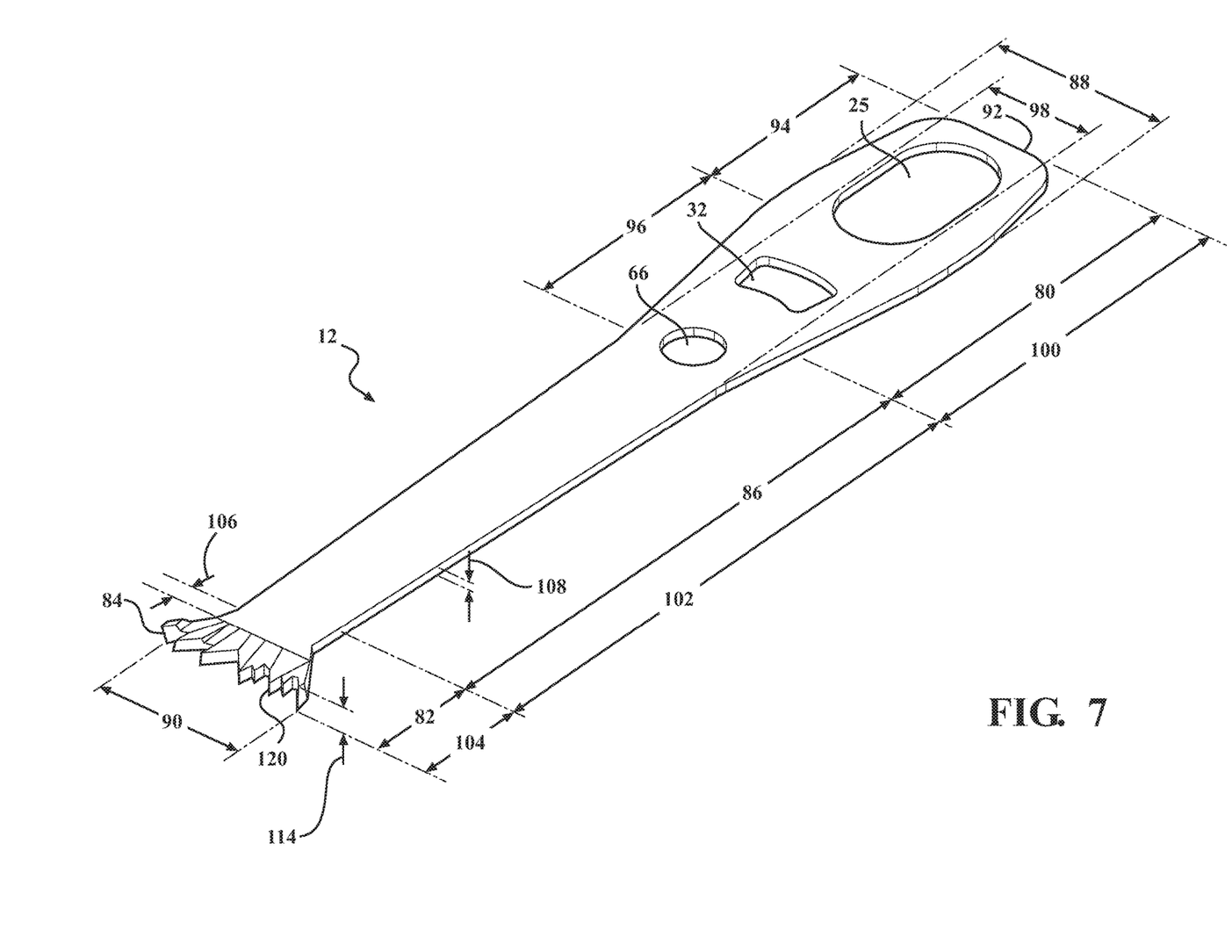
FIG. 7 is a perspective view of a top side of a blade of the surgical saw assembly.
Figure 8:
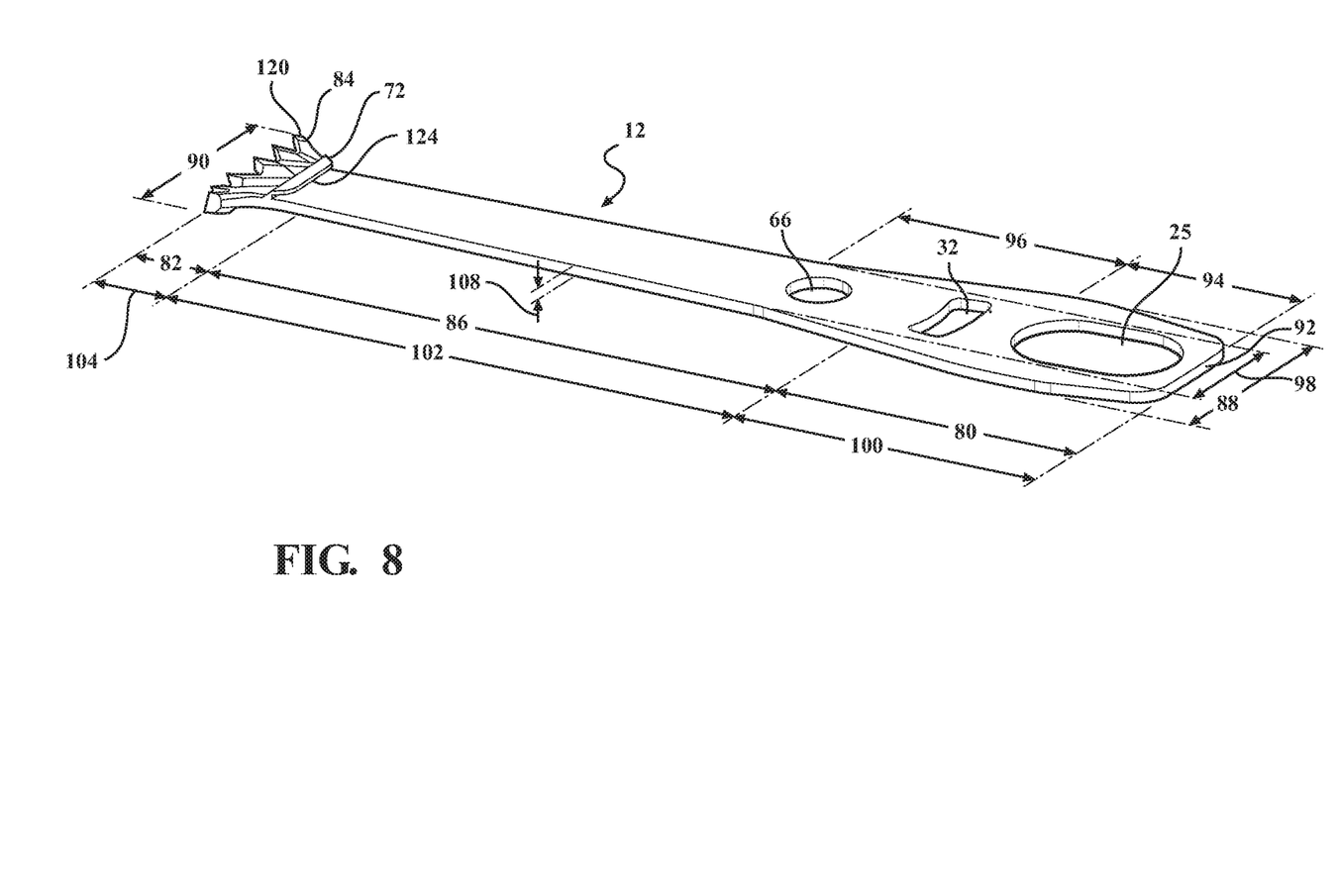
FIG. 8 is a perspective view of a bottom side of the blade of the surgical saw assembly.

Referring to FIGS. 7 and 8, the blade 12 includes an attachment portion 80 configured to be removably coupled to the driver 20. Opposite the attachment portion 80, the blade 12 includes a cutting portion 82 which has a plurality of teeth 84. A pivot portion 86 extends between the attachment portion 80 and the cutting portion 82. The attachment portion 80 of the blade 12, in the embodiment shown, generally has a width 88 greater than a width 90 of the cutting portion 82. In other versions, the widths 88, 90 may be substantially equal or the width 90 may be greater than the width 88. Each of the attachment portion 80, pivot portion 86, and cutting portion 82 may have varying widths. The reference numbers related to blade width are designated as the widest parts of each portion, i.e., the width 88 of the attachment portion 80 is designated at the widest part of the attachment portion 80.

It is contemplated that a length 100 of the attachment portion 80 is less than a length 102 of the pivot portion 86, however, many other configurations have been contemplated. Moreover, a length 104 of the cutting portion 82 may be less than the length 100 of the attachment portion 80 and less than the length 102 of the pivot portion 86.

The attachment portion 80 includes the proximal end 92 and a tapered section 94 which gradually gets wider until it reaches its widest point before tapering back inward at a transition section 96 which partially overlaps the attachment portion 80 and the pivot portion 86. The attachment portion 80 also includes the hub aperture 25 which is configured to receive the drive hub 22, as described above, and the lid aperture 32 which is configured to receive the protrusion 30 of the lid 28, as also described above. The lid aperture 32 has a size and shape such that the protrusion 30 of the lid 28 does not contact the blade 12 during operation of the surgical saw assembly 10. In the embodiment illustrated in FIG. 7, the lid aperture 32 is generally rectangular and may include curved edges. However, it is contemplated that the lid aperture 32 may be any size and shape which prevents the protrusion 30 of the lid 28 from contacting the blade 12 during operation of the surgical saw assembly. In some cases, contact between the protrusion 30 and the blade 12 may be acceptable.

The pivot portion 86 may have a continuous width from the transition section 96 to the cutting portion 82 or the pivot portion 86 may gradually taper in width as the pivot portion 86 approaches the cutting portion 82. The pivot portion 86 includes the pivot aperture 66 disposed through the blade 12. The pivot aperture 66 is configured to receive the pivot structure 64, as described above. Outer side surfaces of the blade 12 at the attachment portion 80 and the pivot portion 86 may be perpendicular to top and bottom surfaces of the blade 12.

A second transition section 106 (see FIG. 7) may be disposed adjacent to the teeth 84 of the cutting portion 82. The second transition section 106 may have a different, typically smaller, width than a width 90 of the cutting portion 84 and a width 98 of the pivot portion 86.

The blade 12 is generally elongate in shape. Additionally, the blade 12 has a weight of from 5-100 grams, from 5-50 grams, from 8.5-30 grams, from 9.0-15.0 grams, from 9.0-12.0 grams, and in some embodiments may have a weight of approximately 9.21 grams. In some embodiments, the blade 12 is formed from a single piece of material, such as metal, by stamping and/or machining.

Figure 9:
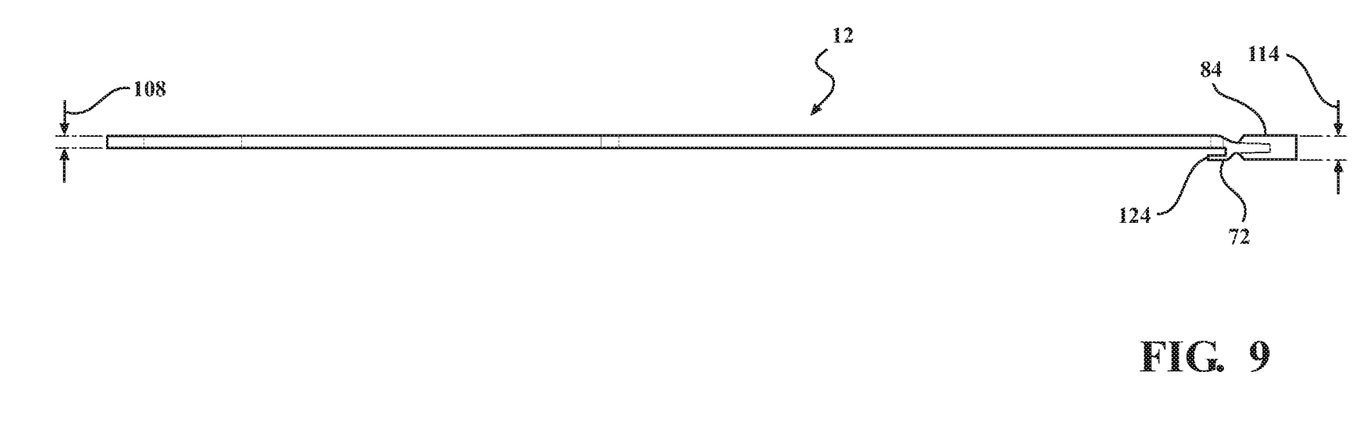
FIG. 9 is a side view of the blade of the surgical saw assembly.
Figure 10:
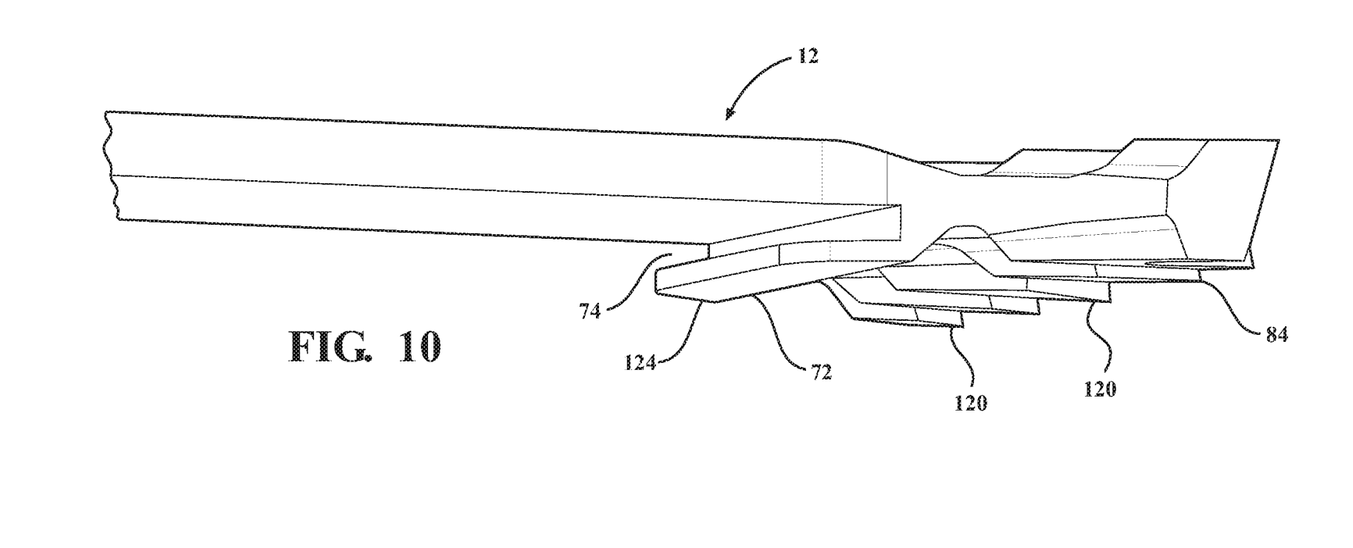
FIG. 10 is a side perspective view of a portion of the blade of the surgical saw assembly.

It is contemplated that the thickness 108 of the blade 12 is a constant thickness on the attachment portion 80 and the pivot portion 86, as illustrated in FIG. 9. Other variations have also been contemplated. Moreover, referring to FIG. 4B, it is contemplated that the thickness 108 of the attachment portion 80 or pivot portion 86 of the blade 12 is less than or equal to a depth 117 of the channel 52 such that the blade 12 does not extend above the shoulder 62 when seated in the channel 52.

Figure 6:
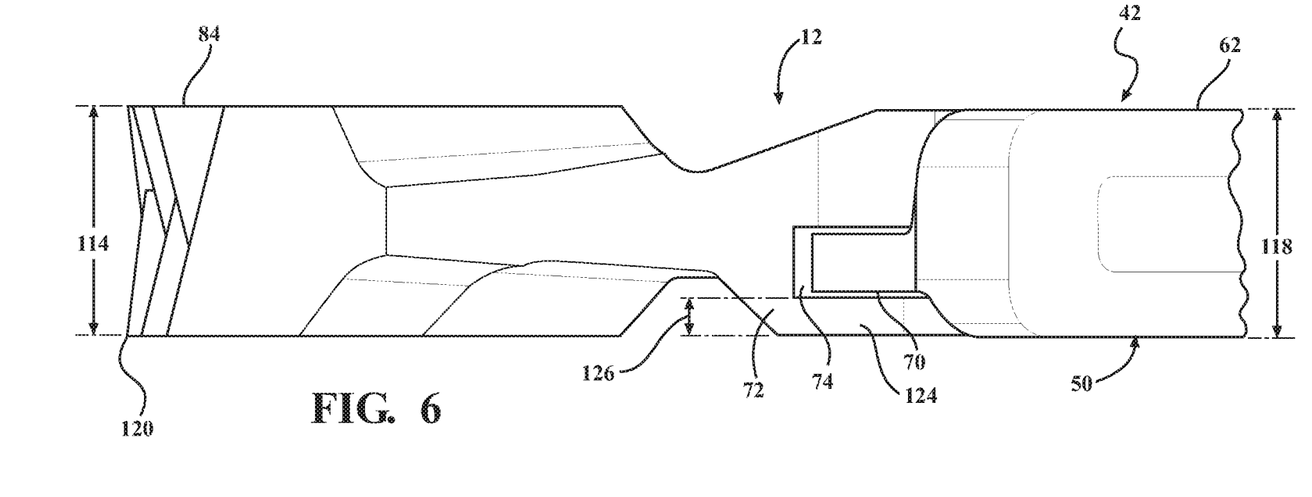
FIG. 6 is a side view of a portion of the surgical saw assembly.

As illustrated in FIG. 6, a thickness 118 of the blade support 42 is defined as the thickness from the bottom surface 50 of the blade support 42 to the top of the shoulder 62. The thickness 118 of the blade support 42 is less than or equal to the thickness 114 of the cutting portion 82. Generally, the greatest thickness 114 of the cutting portion 82 is greater than or equal to the thickness 118 of the blade support 42 so that the blade support 42 is able to follow the cutting portion 82 into material being cut with little interference.

The teeth 84 have generally triangularly shaped profiles and may vary in size. Moreover, the teeth 84 may vary in thickness from one another. Additionally, it is contemplated that a single tooth 120 may have a varied thickness and may taper in thickness from its base to its tip. Each tooth 120 may have an angled cutting edge so that a width of the tooth 120 when viewed from a top view is less than a width of the same tooth 120 when viewed from a bottom view. As illustrated in FIG. 5, the teeth 84 extend past the support flange 70 such that at least a portion of the blade 12 extends past the blade support 42.

The angled cutting edge of each tooth 120 may be configured to provide a cutting advantage in one direction of motion, while an angled cutting edge of an adjacent tooth 120 provides a cutting advantage in an opposite direction. For instance, some teeth 84 may cut best in one direction, while others cut best in the opposite direction. Additionally, some adjacent teeth 84 may be at least partially offset in a direction of the thickness 114 of the cutting portion 82 of the blade 12 so that the tips of the teeth 84 are staggered.

The cutting portion 82 of the blade 12 also includes the follower 72. As best illustrated in FIGS. 5 and 6, the follower 72 extends approximately perpendicular from the bottom surface of the blade 12 and includes a parallel projection in the form of a lip 124 that extends approximately parallel with the pivot portion 86 of the blade 12 to define a space 74. The follower 72 is sized and configured such that gaps are located on either side of the support flange 70 between the support flange 70 and the blade 12 which helps limit wear on the support flange 70 during cutting. The support flange 70 may be formed of harder material than the rest of the blade support 42 and/or may be formed of low friction material and/or coated to reduce wear. Alternatively, or additionally, the support flange 70 may be a replaceable component of the blade support 42. The follower 72 is located in close proximity to the teeth 84 to control a cutting edge as described herein.

During operation of the surgical saw assembly 10, the support flange 70 of the blade support 42 is configured to provide interference so the cutting portion 82 of the blade 12 does not lift away from the blade support 42. More specifically, the follower 72 is configured to ride along the support flange 70 to limit deflection of the blade 12 and to control the cutting edge. In the embodiment illustrated in FIGS. 5 and 6, the flange 70 is captured by the lip 124 of the follower 72 so that the lip 124 rides along the support flange 70 of the blade support 42. The follower 72 is disposed adjacent to the teeth 84. Additionally, it is contemplated that a thickness 126 of the projection 124 is such that a bottom surface of the projection 124 is in plane with the bottom surface 50 of the blade support 42.

In operation, the blade 12 is placed onto the blade support 42 with the follower 72 engaged with the support flange 70 of the blade support 42. Once the follower 72 is correctly placed, the remainder of the blade 12 may be placed onto the blade support 42 with the drive hub 22 disposed through the hub aperture 25 and the pivot structure 64 disposed through the pivot aperture 66. Once the blade 12 is placed in the correct position, the lid 28 is moved to the closed position 34 where the protrusion 30 of the lid 28 is disposed through the securing aperture 32 to hold the blade 12 on the blade support 42. The surgical saw assembly 10 is then powered which may oscillate the blade 12 and/or may otherwise rotate the blade 12 about the axis of blade rotation 26 within the channel 52. During operation, the blade 12 pivots about the pivot structure 64. Opposite the attachment portion 80, the follower 72 of the cutting portion 82 controls the cutting edge by riding along the support flange 70 as the blade 12 pivots about the pivot structure 64.

Figure 11:
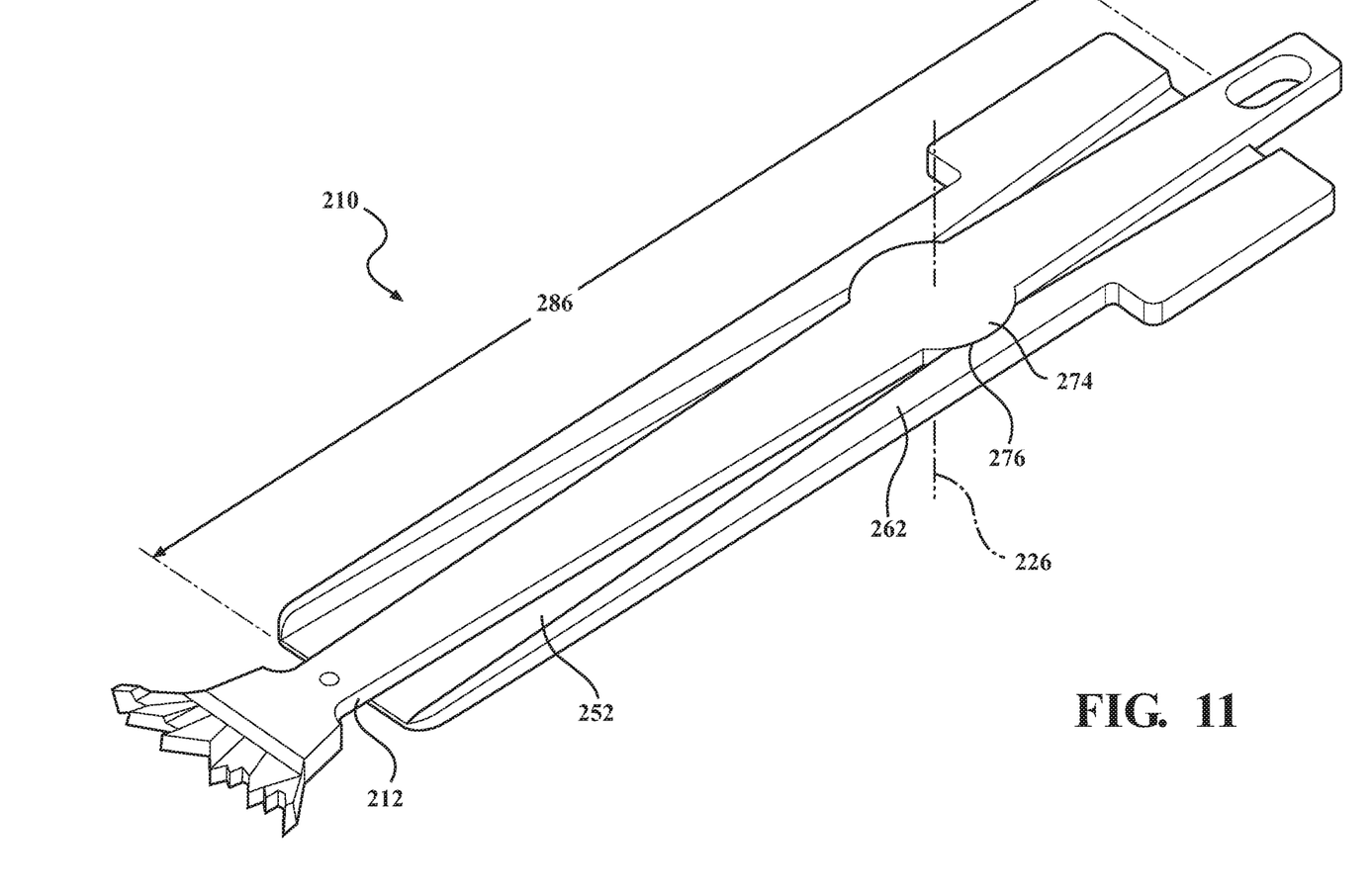
FIG. 11 is a perspective view of an alternative embodiment of the blade and a blade support.

Referring now to the embodiment illustrated in FIG. 11, the surgical saw assembly 210 may have many similar features as described above with respect to the surgical saw assembly 10 illustrated in FIGS. 1-6 including but not limited to the blade 12, the blade support 42, and the channel 52. However, in the embodiment illustrated in FIG. 11, the pivot portion 286 of the blade 212 includes two rounded sections 274 which engage rounded cut outs 276 disposed on each side of the channel 252 defined by shoulder 262. It is contemplated that additional elements may be placed in the cut outs 276 to reduce wear on the blade 212 such as ball bearings, additional and/or different material, and the like. In one embodiment, the two rounded sections 274 are lined up forming at least a partial circle. In other embodiments, the two rounded sections 274 are offset from one another along the axis of rotation 226. Moreover, in the embodiment illustrated in FIG. 11, the two rounded sections 274 are identical. However, various other configurations have been contemplated. The rounded sections 274 of the pivot portion 286 of the blade 212 are configured to pivot within the rounded cut outs 276 during rotational movement about the axis of rotation 226. This configuration allows the pivoting movement of the blade 212 without the use of the pivot structure 64 of the blade support 42.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical saw blade for being coupled to a drive hub of a surgical saw assembly, said blade comprising:
    an attachment portion configured to be removably coupled to the drive hub;
    a cutting portion opposite said attachment portion including a plurality of teeth;
    a pivot portion configured to engage a pivot structure of the surgical saw assembly,
    said cutting portion having a follower which is configured to engage a blade support of the surgical saw assembly and is configured to limit deflection of the blade, wherein said follower includes a projection which extends parallel to said pivot portion.

2. The surgical saw blade of claim 1, wherein said follower is disposed between said pivot portion and said plurality of teeth.

3. The surgical saw blade of claim 2, wherein said follower is disposed adjacent to said plurality of teeth.

4. The surgical saw blade of claim 1, wherein said follower comprises a lip configured to ride along a support flange of the blade support.

5. The surgical saw blade of claim 1, wherein said plurality of teeth have varied thicknesses.

6. The surgical saw blade of claim 1, wherein a single tooth of said plurality of teeth has a varied thickness.

7. The surgical saw blade of claim 1, wherein said plurality of teeth are arranged to extend past the blade support when said cutting portion engages the blade support.

8. A surgical saw assembly comprising:
    a housing;
    a driver disposed within said housing and having a drive hub, said driver configured to be coupled to a motor;
    a blade support including a pivot structure;
    a blade configured to be removably coupled to said drive hub at an attachment portion, said blade comprising a cutting portion opposite said attachment portion and including a plurality of teeth, a pivot portion configured to be coupled to said pivot structure, wherein said cutting portion has a follower configured to engage said blade support to limit deflection of said blade wherein said follower includes a projection which extends parallel to said pivot portion.

9. The surgical saw assembly of claim 8, wherein said follower is disposed between said pivot portion and said plurality of teeth.

10. The surgical saw assembly of claim 9, wherein said follower is disposed adjacent to said plurality of teeth.

11. The surgical saw assembly of claim 8, wherein said blade support comprises a support flange and said follower comprises a lip configured to ride along said support flange of said blade support.

* * * * *